US011490862B2

(12) United States Patent
DeHennis et al.

(10) Patent No.: US 11,490,862 B2
(45) Date of Patent: Nov. 8, 2022

(54) ANALYTE MONITORING SYSTEM AND METHOD FOR DETERMINING SYSTEM USAGE

(71) Applicant: Senseonics, Incorporated, Germantown, MD (US)

(72) Inventors: Andrew DeHennis, Germantown, MD (US); Barbara Montgomery, Gaithersburg, MD (US)

(73) Assignee: Senseonics, Incorporated, Germantown, MD (US)

( * ) Notice: Subject to any disclaimer, the term of this patent is extended or adjusted under 35 U.S.C. 154(b) by 99 days.

(21) Appl. No.: 16/188,736

(22) Filed: Nov. 13, 2018

(65) Prior Publication Data

US 2019/0142345 A1    May 16, 2019

Related U.S. Application Data

(60) Provisional application No. 62/585,006, filed on Nov. 13, 2017.

(51) Int. Cl.
  *A61B 5/00*      (2006.01)
  *G16H 40/40*    (2018.01)
  *G16H 10/60*    (2018.01)
  *A61B 5/145*    (2006.01)

(52) U.S. Cl.
  CPC .......... *A61B 5/7225* (2013.01); *A61B 5/0002* (2013.01); *A61B 5/0022* (2013.01); *A61B 5/145* (2013.01); *A61B 5/14532* (2013.01); *A61B 5/4833* (2013.01); *A61B 5/742* (2013.01); *G16H 40/40* (2018.01); *A61B 2560/028* (2013.01)

(58) Field of Classification Search
  CPC . A61B 5/7225; A61B 5/14532; A61B 5/4833; A61B 5/0022; A61B 5/742; A61B 5/0002; A61B 5/145; A61B 2560/028; G16H 40/40; G16H 10/60
  See application file for complete search history.

(56) References Cited

U.S. PATENT DOCUMENTS

| | | |
|---|---|---|
| 8,073,548 B2 | 12/2011 | Colvin, Jr. et al. |
| 9,414,775 B2 | 8/2016 | Colvin, Jr. et al. |
| 9,693,714 B2 | 7/2017 | DeHennis et al. |
| 10,610,642 B2 * | 4/2020 | Kamath ............ A61B 5/14546 |

(Continued)

FOREIGN PATENT DOCUMENTS

WO    2016/191715 A1    12/2016

*Primary Examiner* — Devin B Henson
*Assistant Examiner* — Justin Xu
(74) *Attorney, Agent, or Firm* — Rothwell, Figg, Ernst & Manbeck, P.C.

(57) ABSTRACT

A method for determining the average usage of an analyte monitoring system may include the step of calculating one or more analyte measurements of a host during a first period of time. The method may include the step of calculating a duration of time that the host uses the analyte monitoring system during the first period of time. The method may include the step of calculating an average time that the host uses the analyte monitoring system during a second period of time or a percentage of the first period of time that the host uses the analyte monitoring system, in which the average time or the percentage is calculated based on at least the calculated duration. The method may include the step of generating and displaying a report indicating the average time or the percentage.

8 Claims, 9 Drawing Sheets

(56) References Cited

U.S. PATENT DOCUMENTS

| | | | |
|---|---|---|---|
| 10,772,503 B2* | 9/2020 | Raisoni | A61B 5/0022 |
| 2002/0019586 A1* | 2/2002 | Teller | A61B 5/02055 |
| | | | 128/903 |
| 2002/0193679 A1* | 12/2002 | Malave | A61M 5/172 |
| | | | 600/407 |
| 2008/0125636 A1* | 5/2008 | Ward | A61B 5/14532 |
| | | | 600/365 |
| 2009/0326357 A1* | 12/2009 | Weinert | G16H 20/17 |
| | | | 600/365 |
| 2010/0331627 A1 | 12/2010 | Thukral et al. | |
| 2010/0331654 A1* | 12/2010 | Jerdonek | G16H 10/60 |
| | | | 600/365 |
| 2011/0004085 A1* | 1/2011 | Mensinger | A61B 5/681 |
| | | | 600/365 |
| 2011/0105979 A1* | 5/2011 | Schlaeper | A61B 5/7475 |
| | | | 600/300 |
| 2011/0126188 A1* | 5/2011 | Bernstein | G06F 8/61 |
| | | | 718/100 |
| 2012/0245446 A1* | 9/2012 | Amann-Zalan | G16H 50/50 |
| | | | 600/365 |
| 2013/0241745 A1 | 9/2013 | Colvin, Jr. et al. | |
| 2014/0200426 A1* | 7/2014 | Taub | A61B 5/14532 |
| | | | 600/347 |
| 2014/0278124 A1* | 9/2014 | Rees | G16H 50/30 |
| | | | 702/19 |
| 2015/0099956 A1* | 4/2015 | Emken | A61B 5/0031 |
| | | | 600/365 |
| 2015/0182115 A1* | 7/2015 | DeHennis | A61B 5/14532 |
| | | | 600/316 |
| 2015/0359490 A1* | 12/2015 | Massey | A61B 5/4839 |
| | | | 600/300 |
| 2016/0038077 A1* | 2/2016 | Otto | A61B 5/14532 |
| | | | 600/365 |
| 2017/0290526 A1* | 10/2017 | Bozorgchami | A61B 5/4833 |
| 2017/0319112 A1 | 11/2017 | Schmelzeisen-Redeker et al. | |
| 2018/0226150 A1* | 8/2018 | Hayter | G16H 50/20 |
| 2018/0374561 A1* | 12/2018 | Binier | G16H 10/60 |
| 2019/0133506 A1* | 5/2019 | Ringemann | A61B 5/14546 |

* cited by examiner

ANALYTE MONITORING SYSTEM AND METHOD FOR DETERMINING SYSTEM USAGE

CROSS-REFERENCE TO RELATED APPLICATION

The present application claims the benefit of priority to U.S. Provisional Application Ser. No. 62/585,006, filed on Nov. 13, 2017, which is incorporated herein by reference in its entirety.

BACKGROUND

Field of Invention

The present disclosure relates to an analyte monitoring system and method. More specifically, aspects of the present disclosure relate to determining average usage of the analyte monitoring system.

Discussion of the Background

Analyte monitoring systems may be used to measure analyte levels, such as analyte concentrations. One type of analyte monitoring system is a continuous glucose monitoring (CGM) system. A CGM system measures glucose levels throughout the day and can be very useful in the management of diabetes.

However, patients who use an analyte monitoring system to monitor their analyte levels often fail to comply with their health care providers' instructions (e.g., by not using their analyte monitoring system for extended periods of time). It has been well documented that patients who comply with their health care providers' instructions by consistently using their analyte monitoring system are significantly more likely to maintain their analyte levels within their target range. Accordingly, improved methods and analyte monitoring systems are needed to improve compliance.

SUMMARY

The present invention overcomes the disadvantages of prior systems by providing, among other advantages, an improved analyte monitoring system that allows the usage time of the analyte monitoring system to be monitored and generated as data feedback for evaluating use compliance.

One aspect of the invention may provide a method of determining the average usage of an analyte monitoring system. The method may include the step of calculating one or more analyte measurements during a first period of time. The method may include the step of calculating a duration of time that the host uses the analyte monitoring system during the first period of time. The method may include the step of calculating an average time that the host uses the analyte monitoring system during a second period of time or a percentage of the first period of time that the host uses the analyte monitoring system, in which the average time or the percentage is calculated based on at least the calculated duration. The method may include the step of generating and displaying a report indicating the average time that the host is using the analyte monitoring system or the percentage of the first period of time that the host uses the analyte monitoring system.

The analyte monitoring system may include an analyte sensor and a transceiver. The transceiver may be configured to receive sensor data from the analyte sensor and calculate the one or more analyte measurements using at least the received sensor data.

In some embodiments, the step of calculating the duration of time that the host uses the analyte monitoring system includes comparing a number of analyte measurements calculated by the analyte monitoring system during the first period of time to an expected number of analyte measurements during the first period of time. In some embodiments, the step of calculating the duration of time that the host uses the analyte monitoring system includes tracking an amount of time when the transceiver is operatively linked to the analyte sensor during the first period of time.

In some embodiments, the analyte monitoring system may include a display device. The display device may be configured to receive the one or more analyte measurements from the transceiver, convey the one or more analyte measurements over a network, and display the one or more analyte measurements and the report indicating the average time that the host uses the analyte monitoring system. In some embodiments, the analyte monitoring system may include a remote computing device. The remote computing device may be configured to receive the one or more analyte measurements from the display device over the network and generate the report indicating the average time that the host uses the analyte monitoring system.

One aspect of the invention may provide a non-transitory tangible computer readable medium. The computer readable medium may be configured to, when executed by one or more processors in an analyte monitoring system, cause the analyte monitoring system to calculate a duration of time that a host uses an analyte monitoring system during a first period of time. The computer readable medium may be configured to, when executed by one or more processors in an analyte monitoring system, cause the analyte monitoring system to calculate an average usage time that the host uses the analyte monitoring system during a second period of time or a percentage of the first period of time that the host uses the analyte monitoring system, in which the average time or the percentage is calculated based on the at least the calculated duration. The computer readable medium may be configured to, when executed by one or more processors in an analyte monitoring system, cause the analyte monitoring system to generate a report indicating the average time that the host uses the analyte monitoring system or the percentage of the first time period that the host uses the analyte monitoring system.

One aspect of the invention may provide an analyte monitoring system that includes an analyte sensor, a transceiver, and a display device. The transceiver may be configured to receive sensor data from the analyte sensor, calculate one or more analyte measurements during a first period of time using at least the received sensor data, calculate a duration of time that the host uses the analyte monitoring system during the first period of time, and calculate an average time that the host uses the analyte monitoring system during a second period of time or a percentage of the first period of time that the host uses the analyte monitoring system, wherein the average time or the percentage is calculated based on at least the calculated duration. The display device may be configured to receive and display the one or more calculated analyte measurements from the transceiver and to display a report indicating the average time that the host uses the analyte monitoring system or the percentage of the of first period of time that the host uses the analyte monitoring system.

One aspect of the invention may include a method of determining an average usage of an analyte monitoring system. The method may include the step of calculating, by the analyte monitoring system configured to be used by a host, one or more analyte measurements of the host during a first period of time. The method may include the step of calculating a duration of time that the host uses the analyte monitoring system during the first period of time. The method may include the step of calculating an average time that the host uses the analyte monitoring system during a second period of time or a percentage of the first period of time that the host uses the analyte monitoring system, in which the average time or the percentage is calculated based on at least the calculated duration. The method may include the step of providing, by the data management system, access to the one or more analyte measurements over a network. The method may include the step of receiving, at a remote display device configured to access the data management system over the network, one or more of the calculated analyte measurements and a report indicating the average time that the host uses the analyte monitoring system during the second period of time or the percentage of the first period of time that the host uses the analyte monitoring system. The remote display device may be located remotely from the analyte monitoring system.

In some embodiments, the data management system may comprise a remote computing device configured to receive the one or more analyte measurements from the analyte monitoring system over the network and share the one or more analyte measurements in proprietary format over the network to one or more remote display devices.

These and other embodiments encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
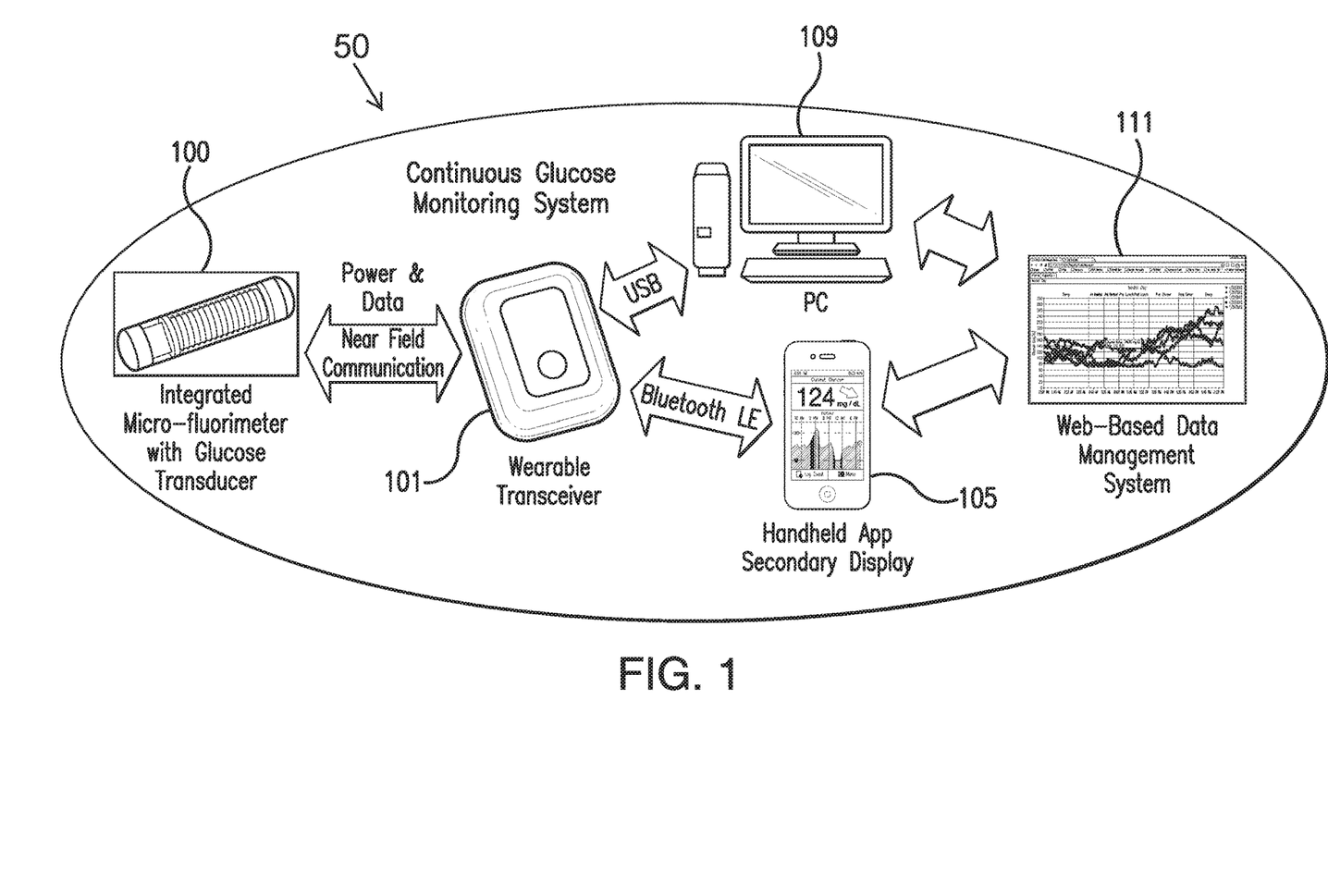
FIG. 1 is a schematic view illustrating an analyte monitoring system embodying aspects of the present invention.

FIG. 1 is a schematic view of an exemplary analyte monitoring system 50 embodying aspects of the present invention. The analyte monitoring system 50 may be a continuous analyte monitoring system (e.g., a continuous glucose monitoring system). In some embodiments, the analyte monitoring system 50 may include one or more of an analyte sensor 100, a transceiver 101, a display device 105, a personal computer 105, and a data management system 111 hosted by a remote server or network attached storage hardware. In some embodiments, the sensor 100 may be small, fully subcutaneously implantable sensor measures analyte (e.g., glucose) concentrations in a medium (e.g., interstitial fluid) of a living animal (e.g., a living human). However, this is not required, and, in some alternative embodiments, the sensor 100 may be a partially implantable (e.g., transcutaneous) sensor or a fully external sensor. In some embodiments, the transceiver 101 may be an externally worn transceiver (e.g., attached via an armband, wristband, waistband, or adhesive patch). In some embodiments, the transceiver 101 may remotely power and/or communicate with the sensor to initiate and receive the measurements (e.g., via near field communication (NFC)). However, this is not required, and, in some alternative embodiments, the transceiver 101 may power and/or communicate with the sensor 100 via one or more wired connections. In some non-limiting embodiments, the transceiver 101 may be a smartphone (e.g., an NFC-enabled smartphone). In some embodiments, the transceiver 101 may communicate information (e.g., one or more analyte concentrations) wirelessly (e.g., via a Bluetooth™ communication standard such as, for example and without limitation Bluetooth Low Energy) to a hand held application running on a display device 105 (e.g., smartphone). In some embodiments, the analyte monitoring system 50 may include a web interface for plotting and sharing of uploaded data.

Figure 2:
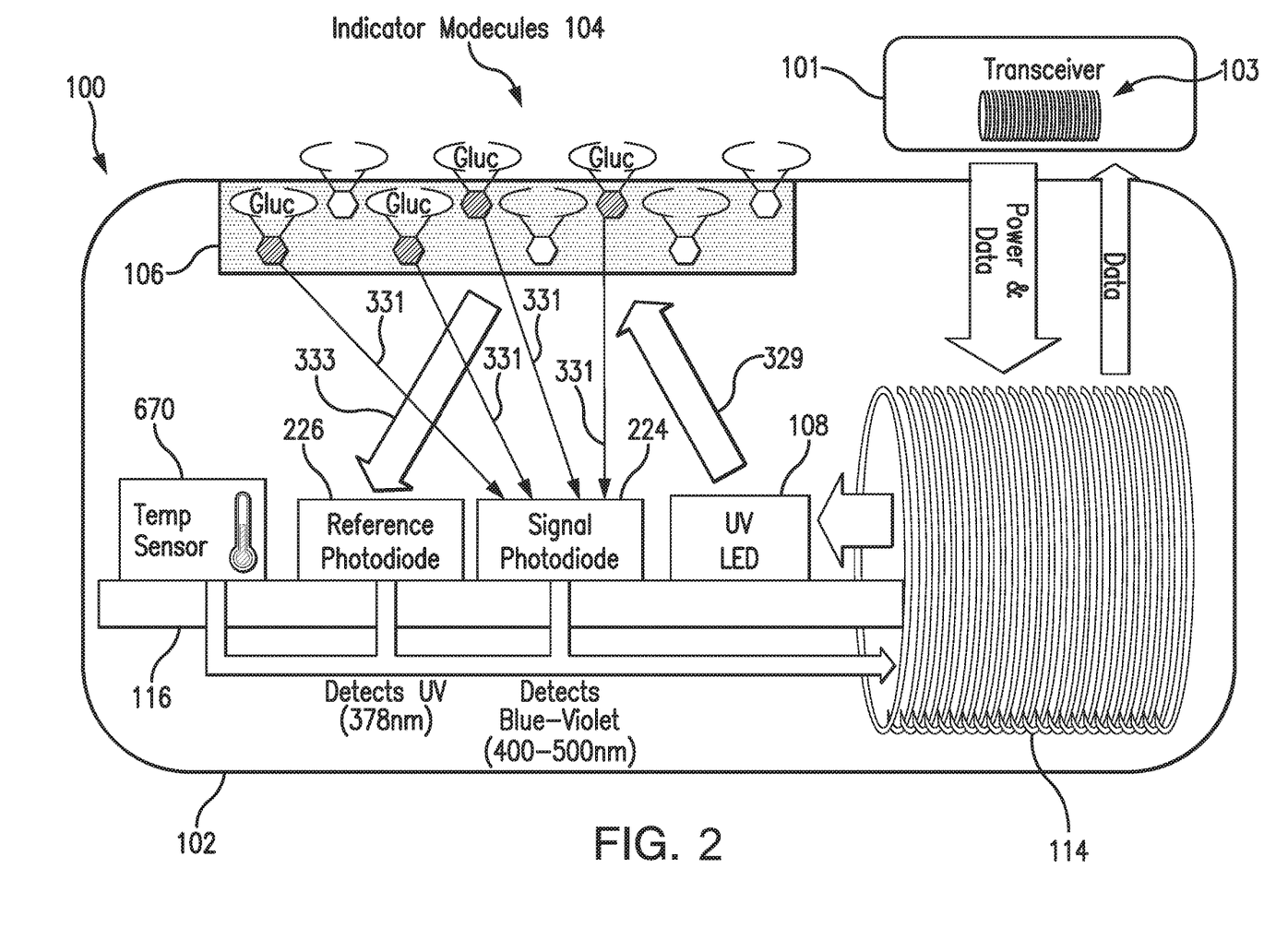
FIG. 2 is a schematic view illustrating a sensor and transceiver of an analyte monitoring system embodying aspects of the present invention.

In some embodiments, as illustrated in FIG. 2, the transceiver 101 may include an inductive element 103, such as, for example, a coil. The transceiver 101 may generate an electromagnetic wave or electrodynamic field (e.g., by using a coil) to induce a current in an inductive element 114 of the sensor 100, which powers the sensor 100. The transceiver 101 may also convey data (e.g., commands) to the sensor 100. For example, in a non-limiting embodiment, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive sensor data (e.g., measurement information) from the sensor 100. For example, in a non-limiting embodiment, the transceiver 101 may receive sensor data by detecting modulations in the electromagnetic wave generated by the sensor 100, e.g., by detecting modulations in the current flowing through the coil 103 of the transceiver 101.

The inductive element 103 of the transceiver 101 and the inductive element 114 of the sensor 100 may be in any configuration that permits adequate field strength to be achieved when the two inductive elements are brought within adequate physical proximity.

In some non-limiting embodiments, as illustrated in FIG. 2, the sensor 100 may be encased in a sensor housing 102 (i.e., body, shell, capsule, or encasement), which may be rigid and biocompatible. The sensor 100 may include an analyte indicator element 106, such as, for example, a polymer graft coated, diffused, adhered, or embedded on or in at least a portion of the exterior surface of the sensor housing 102. The analyte indicator element 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator element 106. In some embodiments, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator element 106 as reflection light 333. In some non-limiting embodiments, one or more of the photodetectors may be covered by one or more filters that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 100 may include a temperature transducer 670. In some non-limiting embodiments, the sensor 100 may include a drug-eluting polymer matrix that disperses one or more therapeutic agents (e.g., an anti-inflammatory drug).

In some embodiments, as illustrated in FIG. 2, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116 and/or a core (e.g., ferrite core) for the inductive element 114. In some embodiments, the semiconductor substrate 116 and/or a core may provide communication paths between the various secured components.

In some embodiments, the one or more of the sensor housing 102, analyte indicator element 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650, 016.

Although in some embodiments, as illustrated in FIG. 2, the sensor 100 may be an optical sensor, this is not required, and, in one or more alternative embodiments, sensor 100 may be a different type of analyte sensor, such as, for example, an electrochemical sensor, a diffusion sensor, or a pressure sensor. Also, although in some embodiments, as illustrated in FIGS. 1 and 2, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, the sensor 100 may include a transceiver interface device. In some embodiments where the sensor 100 includes an antenna (e.g., inductive element 114), the transceiver interface device may include the antenna (e.g., inductive element 114) of sensor 100. In some of the transcutaneous embodiments where there exists a wired connection between the sensor 100 and the transceiver 101, the transceiver interface device may include the wired connection.

Figure 3:
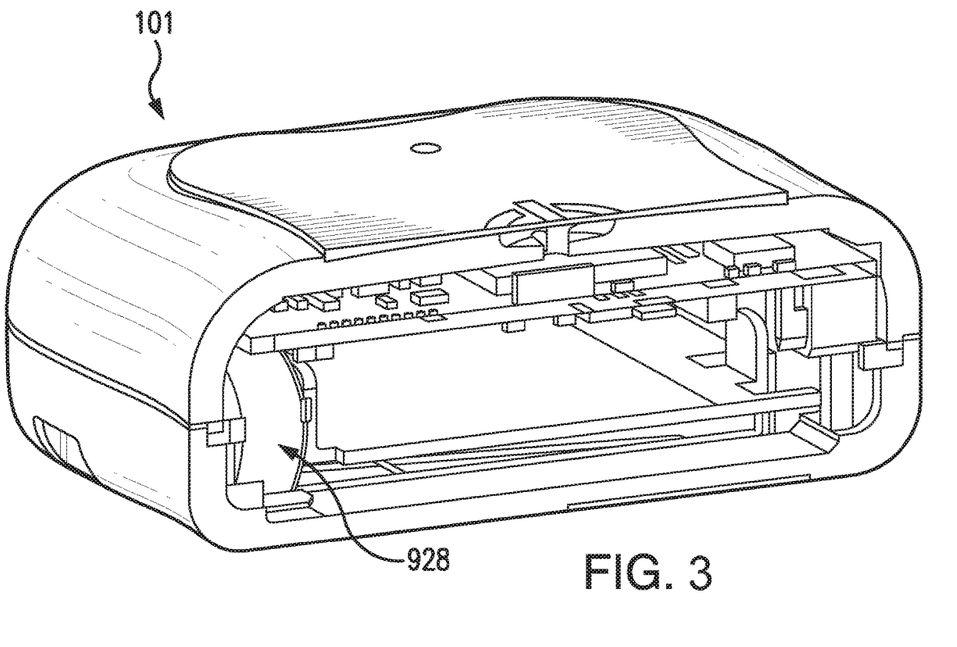
FIG. 3 is cross-sectional, perspective view of a transceiver embodying aspects of the invention.
Figure 4:
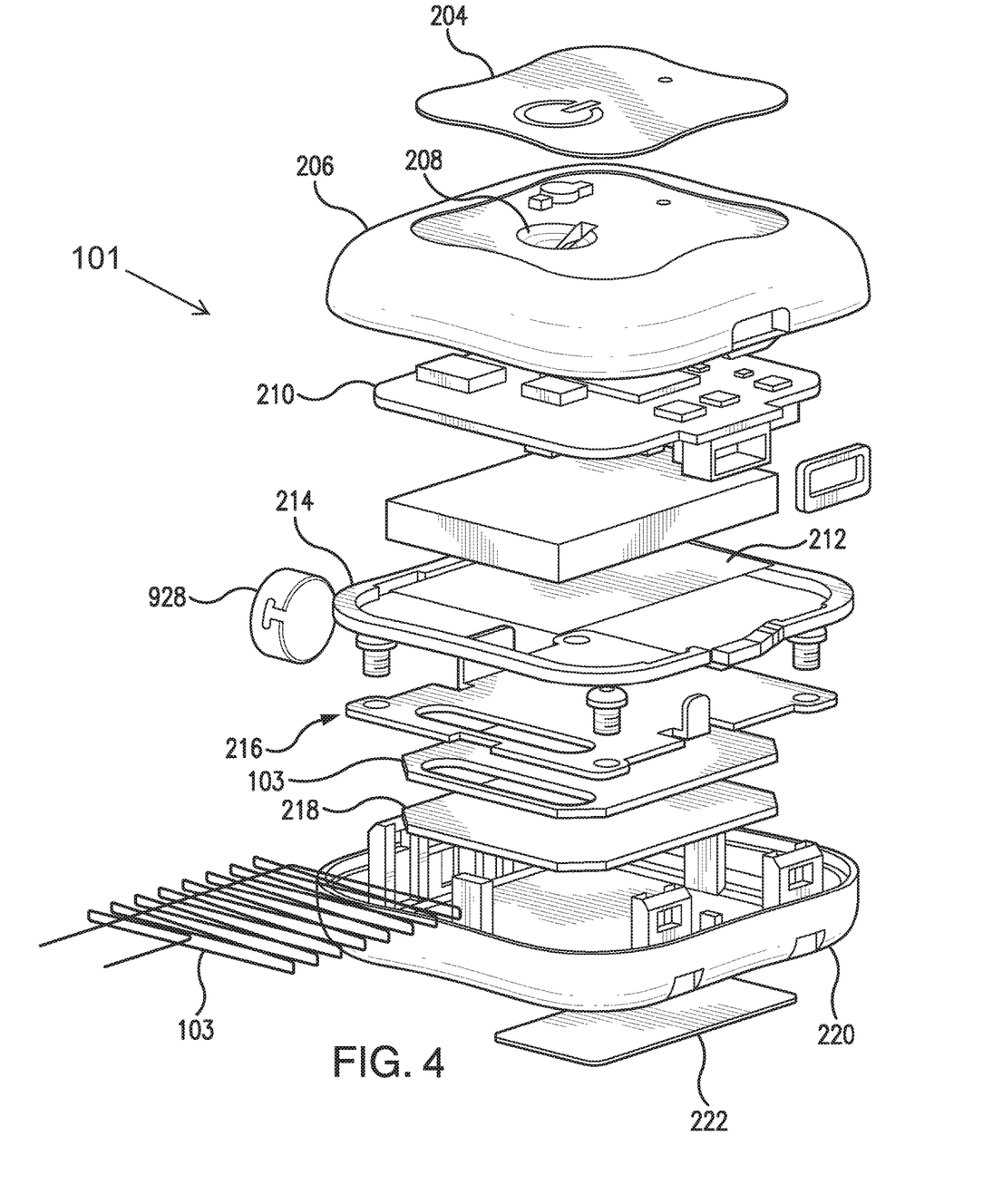
FIG. 4 is an exploded, perspective view of a transceiver embodying aspects of the invention.

FIGS. 3 and 4 are cross-sectional and exploded views, respectively, of a non-limiting embodiment of the transceiver 101, which may be included in the analyte monitoring system illustrated in FIG. 1. As illustrated in FIG. 4, in some non-limiting embodiments, the transceiver 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transceiver electronics may be assembled using standard surface mount device (SMD) reflow and solder techniques. In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transceiver assembly process may be performed at one or more electronics houses, which may be internal, external, or a combination thereof. In some embodiments, the assembled transceiver 101 may be programmed and functionally tested. In some embodiments, assembled transceivers 101 may be packaged into their final shipping containers and be ready for sale.

In some embodiments, as illustrated in FIGS. 3 and 4, the antenna 103 may be contained within the housing 206 and 220 of the transceiver 101. In some embodiments, the antenna 103 in the transceiver 101 may be small and/or flat so that the antenna 103 fits within the housing 206 and 220 of a small, lightweight transceiver 101. In some embodiments, the antenna 103 may be robust and capable of resisting various impacts. In some embodiments, the transceiver 101 may be suitable for placement, for example, on an abdomen area, upper-arm, wrist, or thigh of a patient body. In some non-limiting embodiments, the transceiver 101 may be suitable for attachment to a patient body by means of a biocompatible patch. Although, in some embodiments, the antenna 103 may be contained within the housing 206 and 220 of the transceiver 101, this is not required, and, in some alternative embodiments, a portion or all of the antenna 103 may be located external to the transceiver housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 5:
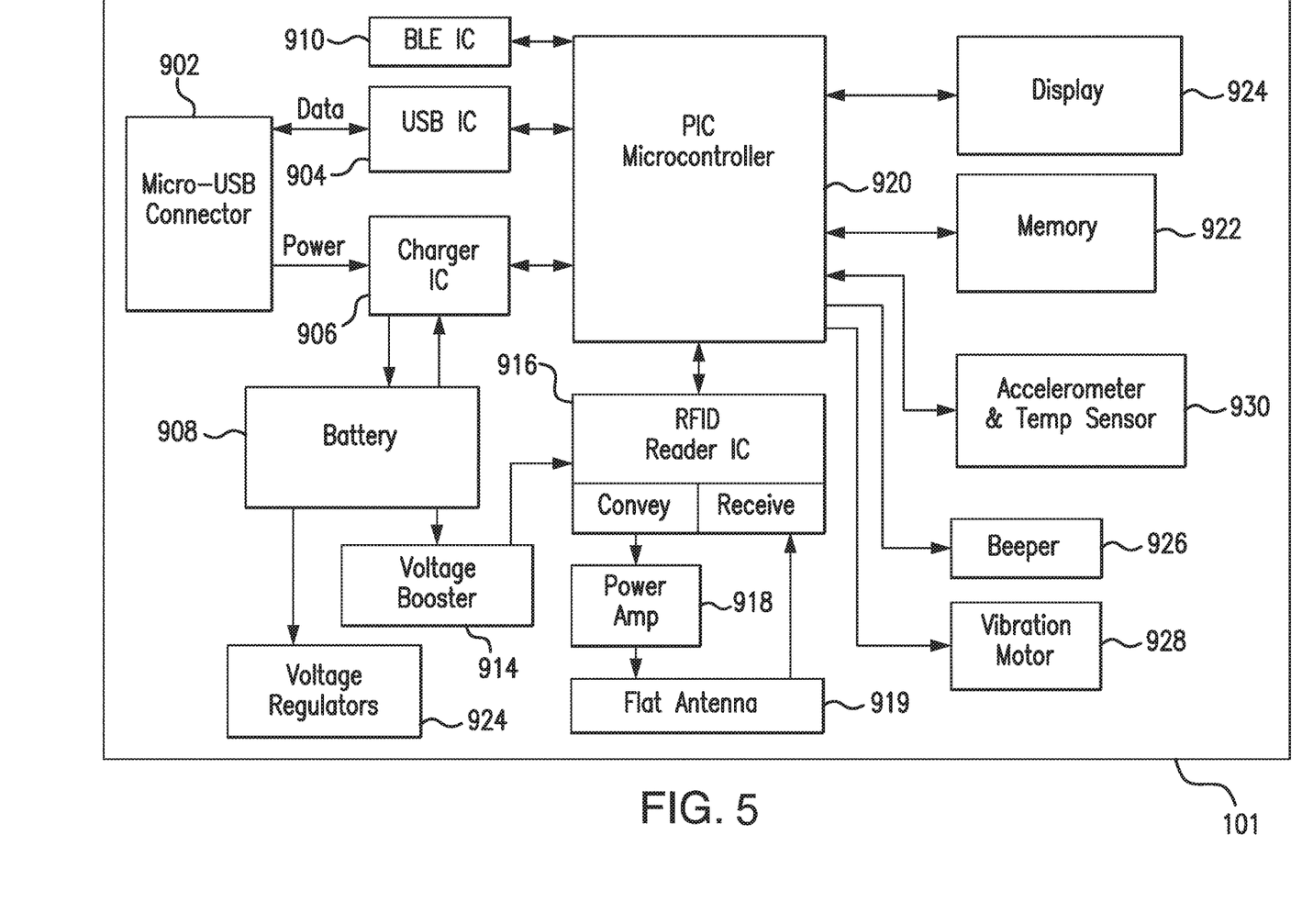
FIG. 5 is a schematic view illustrating a transceiver embodying aspects of the present invention.

FIG. 5 is a schematic view of an external transceiver 101 according to a non-limiting embodiment. In some embodiments, the transceiver 101 may have a connector 902, such as, for example, a Micro-Universal Serial Bus (USB) connector. The connector 902 may enable a wired connection to an external device, such as a personal computer (e.g., personal computer 109) or a display device 105 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer 109) or a display device 105 (e.g., a smartphone) and/or to receive power, which may be used, for example, to charge the battery 908.

In some embodiments, the transceiver 101 may have a wireless communication IC 910, which enables wireless communication with an external device, such as, for example, one or more personal computers (e.g., personal computer 109) or one or more display devices 105 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, the transceiver 101 may include a display interface device, which may enable communication by the transceiver 101 with one or more display devices 105. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In the illustrated embodiment, the inductive element 103 is a flat antenna. In some non-limiting embodiments, the antenna may be flexible. However, as noted above, the inductive element 103 of the transceiver 101 may be in any configuration that permits adequate field strength to be achieved when brought within adequate physical proximity to the inductive element 114 of the sensor 100. In some embodiments, the transceiver 101 may include a power amplifier 918 to amplify the signal to be conveyed by the inductive element 103 to the sensor 100.

The transceiver 101 may include a peripheral interface controller (PIC) microcontroller 920 and memory 922 (e.g., Flash memory), which may be non-volatile and/or capable of being electronically erased and/or rewritten. The PIC microcontroller 920 may control the overall operation of the transceiver 101. For example, the PIC microcontroller 920 may control the connector IC 904 or wireless communication IC 910 to transmit data via wired or wireless communication and/or control the RFID reader IC 916 to convey data via the inductive element 103. The PIC microcontroller 920 may also control processing of data received via the inductive element 103, connector 902, or wireless communication IC 910.

In some embodiments, the transceiver 101 may include a sensor interface device, which may enable communication by the transceiver 101 with a sensor 100. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 100 and the transceiver 101 (e.g., transcutaneous embodiments), the sensor interface device may include the wired connection.

In some embodiments, the transceiver 101 may include a display 924 (e.g., liquid crystal display and/or one or more light emitting diodes), which PIC microcontroller 920 may control to display data (e.g., analyte concentration values). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor, that may be used in the processing performed by the PIC microcontroller 920.

In some embodiments, the transceiver 101 may be a body-worn transceiver that is a rechargeable, external device worn over the sensor implantation or insertion site. The transceiver 101 may supply power to the proximate sensor 100, calculate analyte concentrations from data received from the sensor 100, and/or transmit the calculated analyte concentrations to a display device 105 (see FIG. 1). Power may be supplied to the sensor 100 through an inductive link (e.g., an inductive link of 13.56 MHz). In some embodiments, the transceiver 101 may be placed using an adhesive patch or a specially designed strap or belt. The external transceiver 101 may read measured analyte data from a subcutaneous sensor 100 (e.g., up to a depth of 2 cm or more). The transceiver 101 may periodically (e.g., every 2, 5, or 10 minutes) read sensor data and calculate an analyte concentration and an analyte concentration trend. From this information, the transceiver 101 may also determine if an alert and/or alarm condition exists, which may be signaled to the user (e.g., through vibration by vibration motor 928 and/or an LED of the transceiver's display 924 and/or a display of a display device 105). The information from the transceiver 101 (e.g., calculated analyte concentrations, calculated analyte concentration trends, alerts, alarms, and/or notifications) may be transmitted to a display device 105 (e.g., via Bluetooth Low Energy with Advanced Encryption Standard (AES)-Counter CBC-MAC (CCM) encryption) for display by an application being executed by the display device 105. In other embodiments, the information from the transceiver 101 may be transmitted to a personal computer (PC) 109 or other secondary display devices (not shown) connected over a network.

In some embodiments, the transceiver 101 of the analyte monitoring system 50 may receive raw signals indicative of an amount or concentration of an analyte in proximity to the analyte indicator element 106 of the analyte sensor 100. In some embodiments, the transceiver 101 may receive the raw signals from the sensor 100 periodically (e.g., every 5, 10, or 20 minutes). In some embodiments, the raw signals may include one or more measurements (e.g., one or more measurements indicative of the level of emission light 331 from the indicator molecules 104 as measured by the photodetector 224, one or more measurements indicative of the level of reference light 333 as measured by photodetector 226, and/or one or more temperature measurements as measured by the temperature transducer 670). In some embodiments, the transceiver 101 may use the received raw signals to calculate analyte concentration. In some embodiments, the transceiver 100 may store one or more calculated analyte concentrations (e.g., in memory 922). In some embodiments, the transceiver 100 may convey one or more calculated analyte concentrations to the display device 105, and the display device 105 may display the one or more calculated analyte concentrations.

In some embodiments, the analyte monitoring system 50 may calibrate the conversion of raw signals to analyte concentration. In some embodiments, the calibration may be performed approximately periodically (e.g., approximately every 12 or 24 hours). In some embodiments, the calibration may be performed using one or more reference measurements (e.g., one or more self-monitoring blood glucose (SMBG) measurements), which may be entered into the analyte monitoring system 50 using the user interface of the display device 105. In some embodiments, the transceiver 101 may receive the one or more reference measurements from the display device 105 and perform the calibration. One or more of the reference measurements may be erroneous and may lead to erroneous analyte measurement calculation if used as a calibration point for the calibrating of the conversion of raw sensor data to analyte measurements. Accordingly, the analyte monitoring system 5 (e.g., the transceiver 101) may determine whether to accept (or reject) reference measurements as calibration points in the calibration process. This calibration point acceptance process may be used to prevent erroneous reference measurements from being used as calibration points when calibrating the function used to convert raw sensor data (e.g., light and/or temperature measurements) into analyte measurements (e.g., analyte concentrations). In this way, the calibration point acceptance process may increase the accuracy and/or precision of the analyte measurements.

In some embodiments, the transceiver 101 may store the measurement information received from the sensor 100 (e.g., in memory 922). As noted above, the measurement information received from the sensor 100 may include one or more of: (i) a signal channel measurement with light source 108 on, (ii) a reference or second signal channel measurement with light source 108 on, (iii) a light source current source voltage measurement, (iv) field current measurement, (v) a diagnostic measurement, (vi) an ambient signal channel measurement with light source 108 off, (vii) an ambient reference or second signal channel measurement with light source 108 off, and (viii) a temperature measurement.

In some embodiments, the transceiver 101 may additionally store (e.g., in memory 922) other data with the measurement information received from the sensor 100. In some non-limiting embodiments, the other data may include one or more of: (i) an analyte concentration (e.g., in mg/dL, such as, for example, within a range of 20.0 to 400.0 mg/dL) calculated by the transceiver 101 from the measurement information, (ii) the date and time that the analyte measurement was taken, (iii) accelerometer values (e.g., x, y, and z) taken from an accelerometer of the transceiver 101 (e.g., an accelerometer of additional sensors 930), and/or (iv) the temperature of the transceiver 101 as measured by a temperature sensor of the transceiver 101 (e.g., a temperature sensor of additional sensors 930). In some embodiments, the transceiver 101 may keep track of the date and time and, as noted above, store the date and time along with the received analyte measurement information and/or calculated analyte concentration. In embodiments where the transceiver 101 includes an accelerometer, the accelerometer will enable tracking of activity levels of the subject that is wearing the transceiver 101. This activity level may be included in an event log and incorporated into various algorithms (e.g., for analyte concentration calculation, trending, and/or contributing to potential dosing levels for the subjects). In some embodiments, the transceiver 101 may store (e.g., in memory 922) any alert and/or alarm conditions detected based on the calculated analyte concentrations.

In some embodiments, the transceiver 101 may have a power button (e.g., button 208) to allow the user to turn the device on or off, reset the device, or check the remaining battery life. In some embodiments, the transceiver 101 may have a button, which may be the same button as a power button or an additional button, to suppress one or more user notification signals (e.g., vibration, visual, and/or audible) of the transceiver 101 generated by the transceiver 101 in response to detection of an alert or alarm condition.

Figure 6:
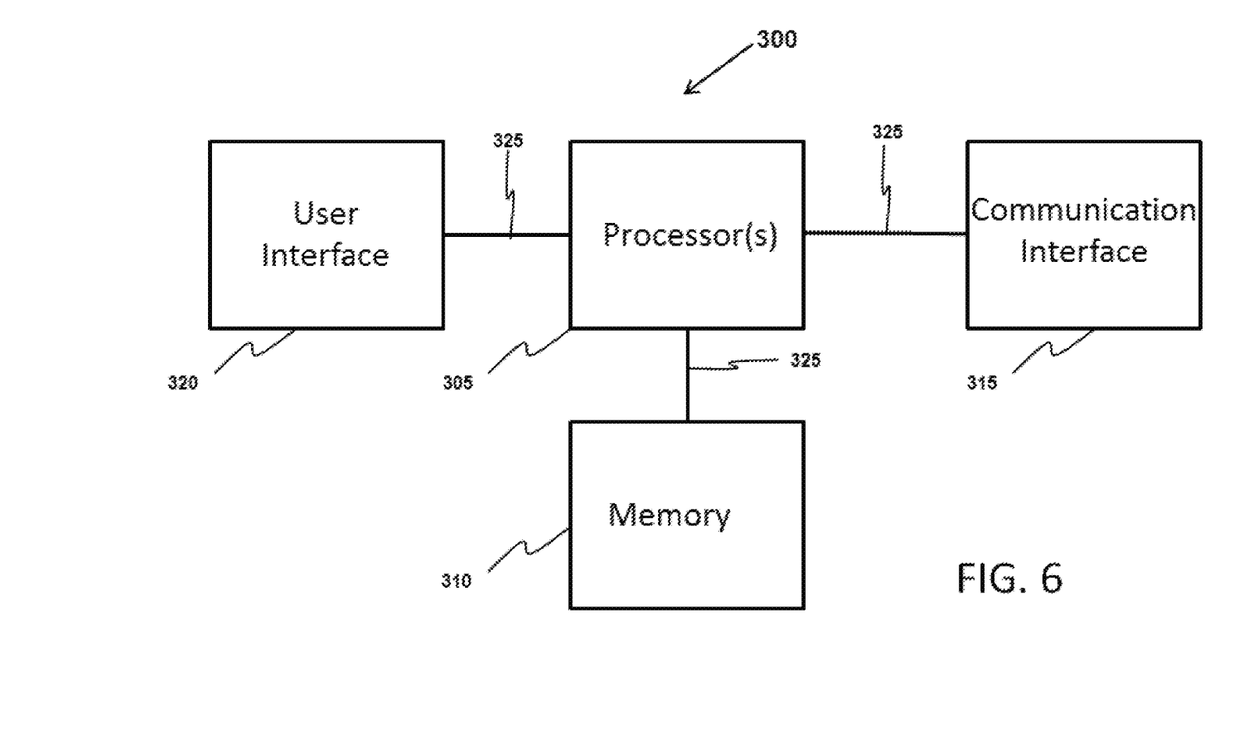
FIG. 6 is a schematic view illustrating a processing system of a display device embodying aspects of the present invention.

In some embodiments, the display device 105 may include a processing system. FIG. 6 illustrates an example of a processing system 300 that may be included in the display device 105. As shown in FIG. 6, the processing system 300 may include one or more processors 305, a memory 310, a communication interface 315, a user interface 320, and/or a bus 325 that couples the various processing system components including the memory 310 to the one or more processors 305. The one or more processors 305 may include one or more central processing units (CPUs) that execute computer program instructions stored in the memory 310 to perform functions described herein with respect to the display device 105. These functions may be configured to improve the technological field of analyte monitoring.

In some embodiments, the memory 310 may include computer storage media in the form of volatile and/or nonvolatile memory, such as ROM and RAM. The system memory 310 may further include non-removable nonvolatile computer storage media, such as a hard disk drive or removable nonvolatile computer storage media that is configured to read from a flash drive, optical disk drive, or other optical media. The drives and their associated computer storage media may provide storage of computer readable instructions, data structures, program modules and other data for the processing system, which are inputted to the one or more processors for the performance of particular tasks.

In some embodiments, the user interface 320 of the processing system 300 may enable an operator to control the device by providing one or more input and/or output devices. The input and/or output devices may include, for example and without limitation, one or more of pushbutton(s), a keyboard, a microphone, a camera, a pointing device (e.g., a mouse, trackball, or touch pad), touch screen(s), voice interfaces(s), multimedia interface(s), audio interface(s), tactile interfaces(s), visual interface(s), and monitor(s). Accordingly, a user may enter commands and information into the device through input devices, and the device may present the analyte information to the user via the output devices. In some embodiments, the communication interface 315 of the processing system 300 may enable the display device to communicate with one or more other devices of the analyte monitoring system.

Figure 7:
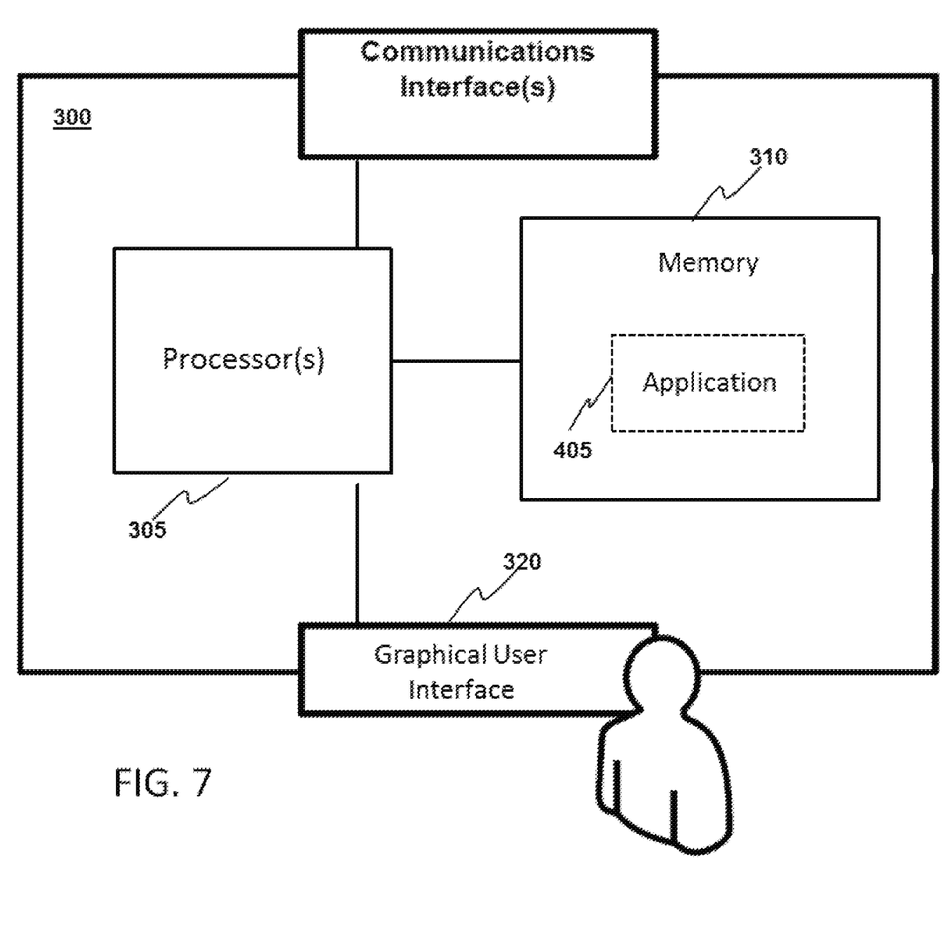
FIG. 7 is a schematic view illustrating a mobile medical application stored in a memory of a processing system of a display device embodying aspects of the present invention.

In some embodiments, as shown in FIG. 7, the memory 310 may store an application 405 in the form of computer readable instructions. In some embodiments, the one or more processors 305 may be configured to execute one or more of the computer readable instructions of the application 405. In some embodiments, where the application 405 may cause the display device 105 to provide a series of graphical control elements or widgets, such as a graphical user interface (GUI), shown on the display of the user interface 320. In some embodiments, the application 405 may, for example and without limitation, cause the display device 105 to display analyte related information in a GUI such as, but not limited to: one or more of analyte information, current analyte readings, user notifications, analyte status alerts and alarms, trend graphs and arrows, and user-entered events, and may provide one or more graphical control elements that may allow a user to manipulate aspects of the one or more display screens.

In some non-limiting embodiments, the application 405 may be a mobile medical application ("MMA"). The MMA may provide alarms, alerts, and/or notifications in addition to any alerts, alarms, and/or notifications received from the transceiver 101. In one embodiment, the MMA may be configured to provide push notifications.

In some embodiments where the system includes the data management system (DMS) 111 (see FIG. 1), the DMS 111 may be a web-based analyte DMS. In some embodiments, the DMS 111 may be a server device employed to allow data to be shared over the network such as the Internet. The server may share data via proprietary formats configured to be employed by hardware computing systems configured, at least in part, with applications to make the hardware computing system into an analyte monitoring system. In some embodiments, data from the display device 105 and/or PC 109 may be uploaded (e.g., through a wired connection such as, for example, a USB connection or a wireless connection such as, for example, a wireless Internet connection) to a web server on a remote computer. In some embodiments, the DMS 111 may enable sharing of the analyte data (e.g., allowing the user, caregiver, and/or clinician to view sensor analyte data). The user may collect analyte data at home or in a clinic/research facility and then upload the data to their computer web account. Using the web account, the DMS 111 may use the data to generate one or more different reports utilizing the uploaded information. For example, in some non-limiting embodiments, the DMS 111 may use the uploaded data to generate one or more of the following reports: (i) an analyte details report, (ii) an analyte line report, (iii) a modal day report, (iv) a modal summary report, (v) a statistics report, and (vi) a transceiver log report.

In some embodiments, a user may use the DMS 111 to register with the DMS 111 and create a unique user ID and password. Once logged in, the user may enter their basic user information and may upload analyte reading data from their transceiver 101. In various embodiments, the DMS 111 may support specific data types such as, for example, glucose, insulin, meal/carbs, exercise, health event, alarms, and errors. In some non-limiting embodiments, data can be automatically uploaded or entered manually by the user or imported from the transceiver 101 and then saved in the DMS 111 to be viewed at a later date.

Figure 8:
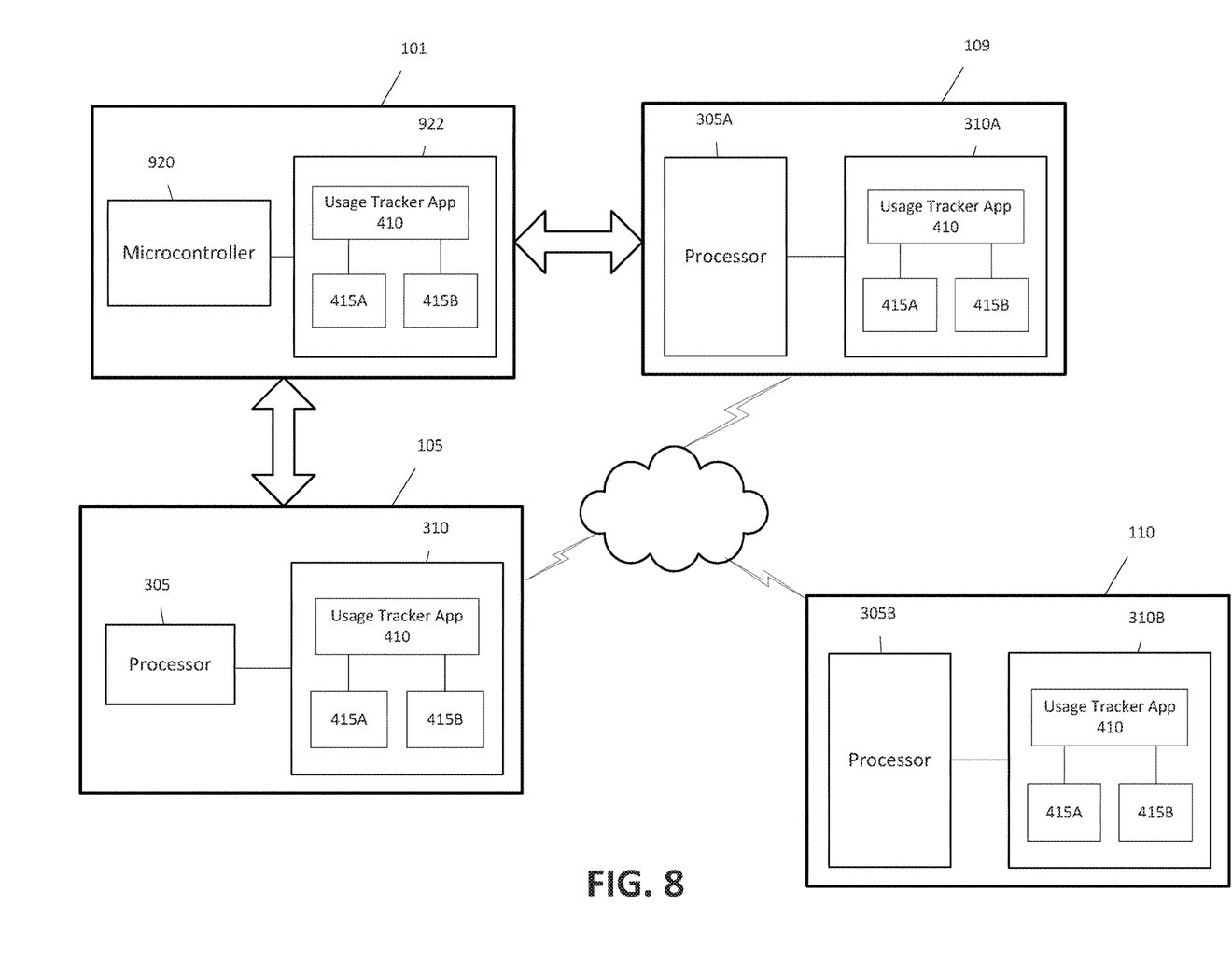
FIG. 8 is a schematic view illustrating a usage tracker application stored in a memory of a processing system of a transceiver, a display device, a personal computer, and a remote server embodying aspects of the present invention.

Referring to FIG. 8, in some embodiments, the analyte monitoring system 50 may include a usage tracker application 410 in the form of computer readable instructions stored in the memory of any one of the transceiver 101, the display device 105, the PC 109, or a remote server 110 linked to the DMS 111. In one embodiment, the usage tracker application 410 may be stored in the memory 922 of the transceiver 101 such that the microcontroller 920 of the transceiver 101 may execute the usage tracker application 410. In one embodiment, the usage tracker application 410 may be stored in the memory 310 of the display device 105 such that the processor 305 of the display device 105 may execute the usage tracker application 410. In one embodiment, the usage tracker application 410 may be incorporated into the mobile medical application 405 such that the mobile medical application 405 and the usage tracker application 410 are executed simultaneously by the processor 305 of the display device 105. In one embodiment, the usage tracker application 410 may be stored in the memory 310A of the personal computer 109 such that the processor 305A of the personal computer 109 may execute the usage tracker application 410. In one embodiment, the usage tracker application 410 may be stored in the memory 310B of the remote server 110 hosting the DMS 111 such that a processor 305B of the remote server 110 may execute the usage tracker application 410.

In some embodiments, when executed by a processor, the usage tracker application 410 may cause the processor to calculate a duration of time that a host uses of the analyte monitoring system 50 during a first period of time. In some embodiments, the host may use the analyte monitoring system 50 by positioning the transceiver 100 such that the transceiver 101 is operatively linked to an analyte sensor 100 implanted in the host. In some non-limiting embodiments, the host may position the transceiver 100 by wearing the transceiver 101 (e.g., using an armband, wristband, belt, or adhesive pad) in proximity to the analyte sensor 100. In some non-limiting embodiments, the host may position the transceiver 100 by swiping the transceiver 101 (e.g., a handheld swipe) in proximity to the analyte sensor 100. In some embodiments, the first period of time may be, for example and without limitation, 1 hour, 2 hours, 6 hours, 12 hours, 1 day, 2 days, 3 days, 1 week, 2 weeks, 1 month, 2 months, 3 months, 6 months, or 1 year. In some non-limiting embodiments, a user of the analyte monitoring system 50 may select or define the first period of time.

In some embodiments, the usage tracker application 410 may cause the processor to calculate an average time that the host uses the analyte monitoring system 50 during a second period of time based on at least the calculated duration of time that the host uses of the analyte monitoring system 50 during the first period of time. In some non-limiting embodiments, the second period of time may be, for example and without limitation, one day. However, this is not required, and, in some alternative embodiments, the second period of time may be a different length of time (e.g., 1 hour, 2 hours, 6 hours, 12 hours, 2 days, 3 days, 1 week, 2 weeks, 1 month, 2 months, 3 months, 6 months, or 1 year). In some non-limiting embodiments, the usage tracker application 410 may additionally or alternatively cause the processor to calculate a percentage of the first period of time that the host uses the analyte monitoring system 50 based on at least the calculated duration of time that the host uses of the analyte monitoring system 50 during the first period of time.

In some embodiments, the usage tracker application 410 may cause the processor to generate and display a report indicating one or more of the average time that the host uses the analyte monitoring system 50 during the second period of time and the percentage of time that the host uses the analyte monitoring system 50 during the first period of time.

In some embodiments, the processor may calculate the duration of time that a host uses of the analyte monitoring system 50 based on one or more algorithms 415A, 415B included in the usage tracker application 410. In some embodiments, the usage tracker application 410 may include a first algorithm 415A that causes the processor to determine the duration of the host's use of the transceiver 101 by comparing the number of analyte measurements calculated by the analyte monitoring system 50 (e.g., by the transceiver 101 of the analyte monitoring system 50) during the first period of time to the number of analyte measurements that were expected to be calculated by the analyte monitoring system 50 during the first period of time. For instance, in a non-limiting example where the first period of time is 168 hours, if 2016 analyte measurements were expected (i.e., one analyte measurement every 5 minutes) and the analyte monitoring system 50 calculated 1512 analyte measurements, the processor may determine that host used the analyte monitoring system 50 for 126 hours during the first period. In some non-limiting embodiments, the expected number of analyte measurements may be derived from the frequency at which the analyte monitoring system 50 calculates analyte measurements (e.g., every 5, 10, or 15 minutes) when the host is using the analyte monitoring system 50. In some embodiments, the analyte measurements calculated by the analyte monitoring system 50 may be stored in a memory (e.g., one or more of memory 922 of the transceiver 101, memory 310 of the display device 105, or memory 310B of the remote server 110 hosting the DMS 111). In some embodiments, the analyte measurements may be stored with a time stamp (e.g., specifying the time at which the transceiver 101 received the sensor data used to calculate the analyte measurement from the analyte sensor 100 or the time at which the analyte monitoring system 50 (e.g., the transceiver 101 of the analyte monitoring system 50) calculated the analyte measurement.

In some non-limiting embodiments, the processor may calculate a ratio between the number of analyte measurements that were calculated by the analyte monitoring system 50 during the first period and the number of measurements that were expected to be calculated by the analyte monitoring system 50 during the first period. In some non-limiting embodiments, the processor may determine the duration of time that the host uses the analyte monitoring system 50 by multiplying the first period of time by the calculated ratio between the actual number of analyte measurements and the expected number of analyte measurements. In some non-limiting embodiments, the analyte monitoring system 50 may display the calculated ratio (or an equivalent percentage).

In some embodiments, the usage tracker application 410 may additionally or alternatively include a second algorithm 415B that causes the processor to determine the duration of time that the host uses the analyte monitoring system 50 by tracking the amount of time when the transceiver 101 is operatively linked to the analyte sensor 100 during the first period of time. In some embodiments, the processor may determine the amount of time based on data reflecting the linkage statuses of transceiver 101 during the first period of time. In one non-limiting embodiment, the second algorithm 415B of the usage tracker application 410 may cause the processor to track each time the status of the transceiver 101 becomes operatively linked to the analyte sensor 100 and each corresponding time when the status of transceiver 101 becomes disconnected from the analyte sensor 100. The processor then may sum up over the first period of time all of the time intervals of the linked connections between the transceiver 101 and the sensor 100 based on the tracked times. The processor may determine the duration of time that the host uses the analyte monitoring system 50 based on the aggregate time intervals over the first period of time.

In some embodiments, the usage tracker application 410 may cause the processor to select one of the algorithms 415A, 415B for calculating the host's use of the analyte monitoring system 50 based on one or more factors so that the duration of the host's use of the analyte monitoring system 50 may be more accurately calculated by the processor. For example, the transceiver 101 may operate under one or more modes, in which the transceiver 101 is operatively linked to the analyte sensor 100 but does not store analyte measurements calculated based on sensor data received from the analyte sensor 100. In one exemplary non-limiting embodiment, the transceiver 101 may not store analyte measurements during a stabilization period, which may occur when the transceiver 101 is initially linked to the analyte sensor 100. In another exemplary non-limiting embodiment, the transceiver 101 may additionally or alternatively not store analyte measurements when the analyte sensor 100 is exposed to high ambient light. In some embodiments, one or more other conditions may additionally or alternatively trigger the transceiver 101 to stop recording measurements, such as a calculated glucose value that is out of range as a high glucose or a low glucose measurement. Consequently, determining an amount to time that the patient uses of the transceiver 101 based on the first algorithm 415A would not take into account the time periods when the host is using the analyte monitoring system 50 (e.g., wearing the transceiver 101) but the transceiver 101 is not recording any measurements.

In some embodiments, the usage tracker application 410 may mitigate the risk of failing to take into account these time periods when the host is using the analyte monitoring system 50 but the transceiver 101 is not storing calculated analyte measurements by basing the selection of the algorithm 415A, 415B on one or more factors. In some embodiments, one factor may correspond to detected periods of time when the transceiver 101 is operatively linked to the analyte sensor 100 but does not store any measurements. The usage tracker application 410 may cause the processor to parse the times and dates of analyte measurements stored in the memory 922 of the transceiver 101 and detect if there are any extended periods of time when the transceiver 101 was operatively linked to the analyte sensor 100 but failed to record any measurements. The detection of the extended period of times may be based on comparing the detected time intervals to a first threshold time interval. If the processor detects any time intervals that exceeds the first threshold time interval, the usage tracker application 410 may cause the processor to select the second algorithm 415B to determine the host's use of the transceiver 101 in order to take into account the times when the transceiver 101 is still worn by the host but not storing measurements received from the analyte sensor.

In some embodiments, the usage tracker application 410 may cause the processor to generate the average time that the host uses the analyte monitoring system 50 based on multiple transceivers 101 or sensors 100 used by the host during the first period of time. For example, if the host uses more than one transceiver 101 during the first period of time (e.g., ninety days), the usage tracker application 410 may cause the processor to aggregate the calculated durations of use for each transceiver 101 and generate the average usage time based on the aggregated durations. Similarly, if the host substitutes a used analyte sensor 100 with a new analyte sensor 100 during the first period of time, the usage tracker application 410 may cause the processor to aggregate the calculated durations of use for each analyte sensor 100 and generate the average usage time based on the aggregated durations. Accordingly, the generated average usage time may take into account the use of multiple transceivers 101 and/or analyte sensors 100 during the first period of time.

Figure 9:
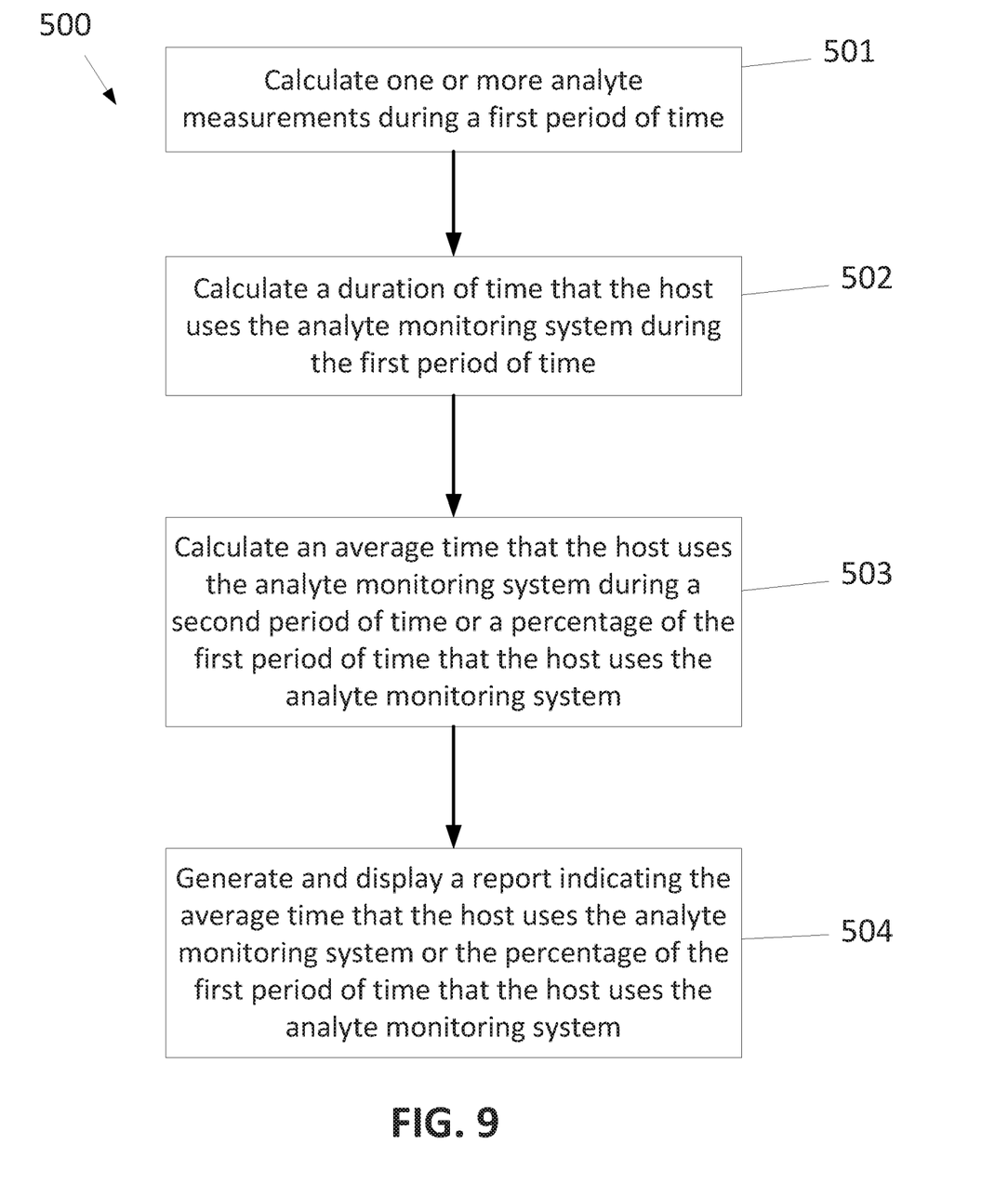
FIG. 9 is a flow chart illustrating a method to determine and display of average wear time of one or more transceivers embodying aspects of the present invention.

FIG. 9 is a flow chart illustrating a process 500 embodying aspects of the present invention. In some embodiments, the process 500 may include a step 501 of calculating, by the analyte monitoring system, one or more analyte measurements of a host during a first period of time. In some embodiments, the process 500 may include a step 502 of calculating a duration of time that the host uses the analyte monitoring system (e.g., positioning the transceiver such that the transceiver is operatively linked to an analyte sensor) during the first period of time. In some embodiments, the step of calculating the duration of the host's use of the analyte monitoring system may include comparing a number of analyte measurements calculated by the analyte monitoring system during the first period of time to an expected number of analyte measurements. In some embodiments, the step of calculating the duration of the host's use of the analyte monitoring system may include tracking an amount of time when the transceiver is operatively linked to the analyte sensor during the first period of time.

In some embodiments, the process 500 may include a step 503 of calculating an average time that the host uses the analyte monitoring system during a second period of time or a percentage of the first period of time that the host uses the analyte monitoring system, in which the average time or percentage is calculated based on at least the calculated duration of step 502. In some embodiments, the average time of use may correspond to the average daily wear time by the host during the second time period. The average daily wear time may be determined by summing up the calculated durations of use from step 502 over a second period of time and dividing the sum of the calculated durations over the number of days in the second period of time.

In some embodiments, the process 500 may include a step 504 of generating and displaying a report indicating the average time that the host uses the analyte monitoring system 50 or the percentage of the first period of time that the host uses the analyte monitoring system. In some embodiments, the reports may be depicted as a line graph, a pie chart, a plot, and the like. In some embodiments, the report screen may further include one or more selectable time interval options that allow a user to adjust the relevant time period for the report. For example, selectable time interval options may include 1 day, 7 days, 14 days, 30 days, and 90 days. However, the embodiments disclosed herein are not limited to these specific time interval options. In some embodiments, reports may indicate both the average time based on calculations derived from the first algorithm 415A and the average time based on calculations derived from the second algorithm 415B. In some embodiments, the reports may include a message indicating a status of the host's compliance with a set goal or standard and encouraging the host to continue to use the analyte monitoring system 50.

In some embodiments, analyte data may be conveyed to the display device 105, in which the analyte data includes the date and time of the recorded analyte measurements and the linkage statuses of the transceiver over a predetermined period of time. Based on the transmitted analyte data, the processor 305 of the display device may generate the report indicating the average time that the host uses the analyte monitoring system 50. The reports may be displayed on the user interface 320 of the display device 105 so that the host may be notified of his or her average usage time of the analyte monitoring system 50. In some embodiments, analyte data may be conveyed to the remote server 110 hosting the DMS 111, in which the analyte data includes the date and time of recorded analyte measurements and the linkage statuses of the transceiver over a period of time. Based on the transmitted analyte data, the processor 305B of the remote server 110 may execute any one of steps 501-504 to generate a report indicating the average time that the host uses the analyte monitoring system 50 or a percentage of the first period of time that the host uses the analyte monitoring system. Accordingly, any device linked to the DMS 111 may gain access to the average usage time reports. For example, a medical personnel may view the average usage time reports of any patients who have uploaded their data to the DMS 111 by linking a personal computer at the clinic to the DMS 111.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

What is claimed is:

1. A method of determining an average usage of an analyte monitoring system, the method comprising:
   using an analyte sensor of the analyte monitoring system to convey sensor data including measurement information;
   using a transceiver of the analyte monitoring system to receive the sensor data conveyed by the analyte sensor;
   using the transceiver to calculate one or more analyte concentrations using at least the received sensor data during a first period of time;
   using the analyte monitoring system to calculate a duration of time that a host uses the analyte monitoring system during the first period of time, wherein calculating the duration of time that the host uses the analyte monitoring system comprises:
      determining a number of analyte concentrations calculated by the analyte monitoring system during the first period of time;
      calculating a ratio between the determined number of analyte concentrations and an expected number of analyte concentrations during the first period of time; and
      multiplying the first period of time by the calculated ratio;
   using the analyte monitoring system to calculate an average time that the host uses the analyte monitoring system during a second period of time, wherein the average time is calculated based on at least the calculated duration; and
   using the analyte monitoring system to generate and display a report indicating the average time that the host uses the analyte monitoring system.

2. The method of claim 1, wherein using the analyte monitoring system includes positioning the transceiver such that the transceiver is operatively linked to the analyte sensor.

3. The method of claim 1, wherein the analyte monitoring system further comprises a display device configured to receive the one or more analyte concentrations from the transceiver, convey the one or more analyte measurements over a network, and display the one or more analyte concentrations and the report.

4. The method of claim 3, wherein the analyte monitoring system further comprises a remote computing device configured to receive the one or more analyte concentrations from the display device over the network and generate the report.

5. A method of determining an average usage of an analyte monitoring system, the method comprising:
   using an analyte sensor of the analyte monitoring system to convey sensor data including measurement information;
   using a transceiver of the analyte monitoring system to receive the sensor data conveyed by the analyte sensor;
   using the transceiver to calculate one or more analyte concentrations using at least the received sensor data during a first period of time;
   using the analyte monitoring system to calculate a duration of time that a host uses the analyte monitoring system during the first period of time, wherein calculating the duration of time that the host uses the analyte monitoring system comprises:
      determining a number of analyte concentrations calculated by the analyte monitoring system during the first period of time;
      calculating a ratio between the determined number of analyte concentrations and an expected number of analyte concentrations during the first period of time; and
      multiplying the first period of time by the calculated ratio;
   using the analyte monitoring system to calculate a percentage of the first period of time that the host uses the analyte monitoring system, wherein the percentage is calculated based on at least the calculated duration; and
   using the analyte monitoring system to generate and display a report indicating the percentage of the first period of time that the host uses the analyte monitoring system.

6. The method of claim 5, wherein using the analyte monitoring system includes positioning the transceiver such that the transceiver is operatively linked to the analyte sensor.

7. The method of claim 5, wherein the analyte monitoring system further comprises a display device configured to receive the one or more analyte concentrations from the transceiver, convey the one or more analyte measurements over a network, and display the one or more analyte concentrations and the report.

8. The method of claim 7, wherein the analyte monitoring system further comprises a remote computing device configured to receive the one or more analyte concentrations from the display device over the network and generate the report.

* * * * *